United States Patent
Lin

(10) Patent No.: US 7,031,767 B2
(45) Date of Patent: Apr. 18, 2006

(54) MOBILE PHONE WITH FAT MEASURING FUNCTION AND THE FAT MEASURING METHOD THEREOF

(75) Inventor: Chih-Lung Lin, Sinying (TW)

(73) Assignee: Benq Corporation, (TW)

( * ) Notice: Subject to any disclaimer, the term of this patent is extended or adjusted under 35 U.S.C. 154(b) by 0 days.

(21) Appl. No.: 10/868,356

(22) Filed: Jun. 16, 2004

(65) Prior Publication Data

US 2005/0020936 A1  Jan. 27, 2005

(30) Foreign Application Priority Data

Jun. 17, 2003 (TW) ............................ 92116470 A

(51) Int. Cl.
*A61B 5/05* (2006.01)

(52) U.S. Cl. .................. 600/547; 379/207.02

(58) Field of Classification Search ............... 600/547, 600/300, 372; 705/2; 128/903, 904, 920, 128/921; 379/207.02, 419, 434, 428.01, 379/433.01, 457
See application file for complete search history.

(56) References Cited

U.S. PATENT DOCUMENTS 5,611,351 A * 3/1997 Sato et al. .................. 600/547
6,327,495 B1 * 12/2001 Iwabuchi et al. ........... 600/547
2001/0030546 A1 * 10/2001 Yamada et al. ............. 324/691
2003/0208409 A1 * 11/2003 Mault .......................... 705/26
2004/0002662 A1 * 1/2004 Hjelt et al. .................. 600/547

FOREIGN PATENT DOCUMENTS

| CN | 1276709 | | 12/2000 |
| JP | 2002095637 | A * | 4/2002 |
| JP | 2003079592 | A * | 3/2003 |
| TW | 521145 | | 2/1998 |
| WO | WO 200176220 | A1 * | 10/2001 |

* cited by examiner

*Primary Examiner*—Charles Marmor
(74) *Attorney, Agent, or Firm*—Rabin & Berdo, PC

(57) ABSTRACT

A mobile phone with fat measuring function including a mobile phone control module, a display device, a fat measuring control circuit, a constant current electrode pair and a voltage measuring electrode pair is provided. Both the display device and the fat measuring control circuit are coupled to the mobile phone control module, while both constant current electrode pair and voltage measuring electrode pair are coupled to the fat measuring control circuit. When the user touches the constant current electrode pair and the voltage measuring electrode pair, the fat measuring control circuit firstly applies a predetermined current to the constant current electrode pair. The predetermined current causes the voltage measuring electrode pair to generate a measured voltage. The user's body fat percentage is then generated according to the measured voltage and the user's weight data, and the body fat percentage is displayed on the display device.

4 Claims, 6 Drawing Sheets

MOBILE PHONE WITH FAT MEASURING FUNCTION AND THE FAT MEASURING METHOD THEREOF

This application claims the benefit of Taiwan application Serial No. 092116470, filed Jun. 17, 2003, the subject matter of which is incorporated herein by reference.

BACKGROUND OF THE INVENTION

1. Field of the Invention

The invention relates in general to a mobile phone, and more particularly to a mobile phone with fat measuring function and the fat measuring method thereof.

2. Description of the Related Art

With the rapid advance in science and technology, mobile phone is playing an important role in people's daily lives. By means of wireless transmission, messages can be transmitted immediately allowing people to have an instant access of the information they require.

Along with the rise of people's awareness of health issues, the use of a fat measuring device is getting more and more popular. Using a fat measuring device to measure body fat percentage, the users can understand his or her body fat percentage so as to arrange their personal health management accordingly. An individual with a high body fat percentage is predisposed to illnesses such as hypertension, heart disease, diabetes, cancers, etc.

However, a conventional fat measuring device can neither provide the user with relevant exercise and diet advices according to the body fat percentage measured nor can a conventional fat measuring device be connected to a medical center for necessary follow-ups. It would conduce to the maintenance of personal health a lot if the information of body fat percentage can be wirelessly transmitted to a medical center via a mobile phone so that the medical professionals can provide instant advices or promptly conduct necessary follow-ups.

SUMMARY OF THE INVENTION

It is therefore an object of the invention to provide a mobile phone with fat measuring function and the fat measuring method thereof. The user can use the mobile phone with fat measuring function according to the invention to measure his or her body fat percentage and have the obtained body fat percentage transmitted to a medical center via wireless transmission. By means of speedy and instant wireless transmission, the user can receive the medical professionals' advices and follow-ups via a mobile phone. The invention really provides the user with timely assistance regarding the maintenance of health.

It is another object of the invention to provide a mobile phone for measuring a user's body fat percentage according to his or her weight data, including a mobile phone control module, a display device, a fat measuring control circuit, a constant current electrode pair and a voltage measuring electrode pair. Both the display device and the fat measuring control circuit are coupled to the mobile phone control module, while both constant current electrode pair and voltage measuring electrode pair are coupled to the fat measuring control circuit. When the user touches the constant current electrode pair and the voltage measuring electrode pair, the fat measuring control circuit applies a predetermined current to the constant current electrode pair. The predetermined current causes the voltage measuring electrode pair to generate a measured voltage. The user's body fat percentage is then generated according to the measured voltage and the user's weight data, and the body fat percentage is displayed on the display device.

It is another object of the invention to provide a fat measuring method performed on a mobile phone, wherein the mobile phone includes a mobile phone control module, a display unit, a fat measuring control circuit, a constant current electrode pair and a voltage measuring electrode pair. Both the display unit and the fat measuring control circuit are coupled to the mobile phone control module, and both the constant current electrode pair and the voltage measuring electrode pair are coupled to the fat measuring control circuit. The fat measuring method according to the invention includes the steps disclosed below. First, the mobile phone control module accesses the user's personal data including at least a weight data. Next, the user touches the constant current electrode pair and the voltage measuring electrode pair, allowing the fat measuring control circuit to measure the bioelectric impedance of the user. Then, the fat measuring control circuit generates a body fat percentage of the user according to the bioelectric impedance and user's personal data and display the body fat percentage on the display device.

Other objects, features, and advantages of the invention will become apparent from the following detailed description of the preferred but non-limiting embodiments. The following description is made with reference to the accompanying drawings.

DETAILED DESCRIPTION OF THE INVENTION

The spirit of the mobile phone with fat measuring function according to the invention and the measuring method thereof lies in providing the mobile phone with fat measuring function so that the user can measure his or her body fat percentage and have the body fat percentage wirelessly transmitted to a medical center wherever and whenever he or she would like to. By means of a mobile phone, the user can even instantly receive professional advices and follow-ups from the medical center. Apart from the abovementioned function, the fat measuring function according to the invention can communicate with the base station to receive a suggested diet which fits the user's needs and is available in nearby restaurants. Furthermore, the body fat percentage obtained using the mobile phone with fat measuring function according to the invention can be used for the purpose of user's identification recognition.

Figure 1:
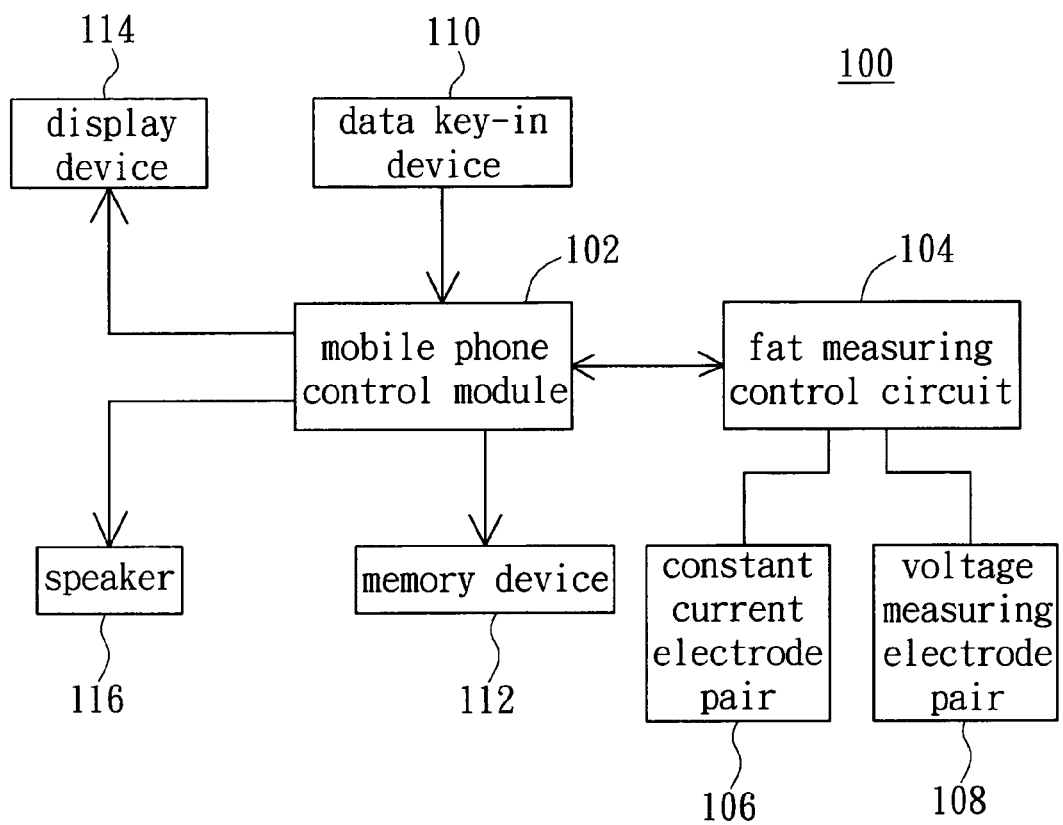
FIG. 1 is a block diagram of the mobile phone with fat measuring function according to a preferred embodiment of the invention.
Figure 2A:
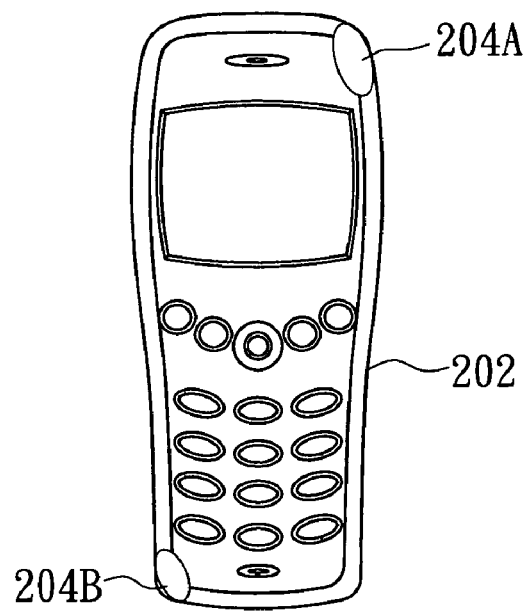
FIG. 2A is a front view of the mobile phone with fat measuring function according to the invention.
Figure 2B:
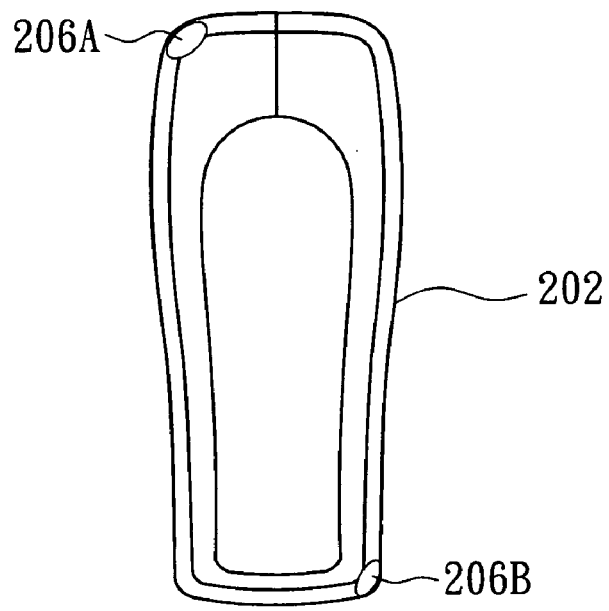
FIG. 2B is a rear view of the mobile phone with fat measuring function according to the invention.

Referring to FIGS. 1, 2A and 2B at the same time, FIG. 1 is a block diagram of the mobile phone with fat measuring function according to a preferred embodiment of the invention, and FIGS. 2A and 2B respectively are the front and the rear views of the mobile phone with fat measuring function according to the invention. Mobile phone with fat measuring function 100 according to the invention includes an outer casing 202, a mobile phone control module 102, a fat measuring control circuit 104, a constant current electrode pair 106, a voltage measuring electrode pair 108, a data key-in device 110, a memory device 112, a display unit 114, and a speaker 116.

Mobile phone control module 102 is used to control mobile phone 100 and to receive/transmit wireless signals. Fat measuring control circuit 104 is coupled to mobile phone control module 102. Constant current electrode pair 106 includes constant current electrodes 204A and 204B, while voltage measuring electrode pair 108 includes voltage measuring electrodes 206A and 206B. Constant current electrodes 204A and 204B are disposed on the front surface of outer casing 202 and are coupled to fat measuring control circuit 104, whereas voltage measuring electrodes 206A and 206B are disposed on the rear of outer casing 202 and are coupled to fat measuring control circuit 104. To avoid signal interference, it is better to keep constant current electrodes 204A and 204B at a fixed distance. Constant current electrodes 204A and 204B are respectively disposed at the top right corner and the bottom left corner of the front surface of outer casing 202, whereas voltage measuring electrodes 206A and 206B are respectively disposed at the rear of outer casing 202 corresponding to constant current electrodes 204A and 204B. According to the above arrangement, constant current electrode 204A and voltage measuring electrode 206A are disposed at the right hand side of the outer casing, while constant current electrode 204B and voltage measuring electrode 206B are disposed at the left hand side of the outer casing. When the user touches electrodes 204A and 206A with his or her right (left) thumb and right (left) index finger respectively and touches electrodes 204B and 206B with his or her left (right) thumb and left (right) index finger respectively, the pictures and texts on the screen of the mobile phone still remain at a readable angle to the user.

Data key-in device 110 is used for the user to input his or her personal data including at least the gender, weight and height, while memory device 112 is used to store these personal data. Display device 114 is used to display inputted personal data of and the obtained body fat percentage of the user. Apart from voicing out caller's dialogue, speaker 116 can be used to remind the user of inputting relevant data and remind the user that the calculation of body fat percentage is completed and is displayed on display device 114.

When the user touches constant current electrodes 204A and 204B and voltage measuring electrode 206A and 206B, fat measuring control circuit 104 generates the user's body fat percentage according to his or her personal data. Preferably, the user should touch constant current electrode pair 106 with his or her thumbs and touch voltage measuring electrode pair 108 with his or her index fingers respectively. For example, the user touches constant current electrode 204A and voltage measuring electrode 206A with right thumb and right index finger respectively and touches constant current electrode 204B and voltage measuring electrode 206B with left thumb and left index finger respectively.

Fat measuring control circuit 104 of mobile phone 100 according to the invention has plural ways of implementation. Fat measuring control circuit 104 mainly uses bioelectric impedance analysis to measure user's fat mass and obtain the user's body fat percentage. The main concept of the method, in which a very weak current, which is safe to the user, is applied to flow through the body, is that while the fat inside the body is almost nonconductive, and the water inside the tissue of the body is conductive, the fat of the body can be estimated according to the user's bioelectric impedance.

Therefore, fat measuring control circuit 104 includes at least a voltage measuring device which is coupled to voltage measuring electrode pair 108, wherein when the user touches constant current electrode pair 106 and voltage measuring electrode pair 108, an alternating current signal flows through the user's body so the voltage measuring device detects a voltage cross voltage measuring electrode pair 108. According to the voltage detected and the weight data inputted, fat measuring control circuit 104 produces a body fat percentage for the user. This is exemplified in a preferred embodiment of fat measuring control circuit 104 disclosed below.

Figure 3:
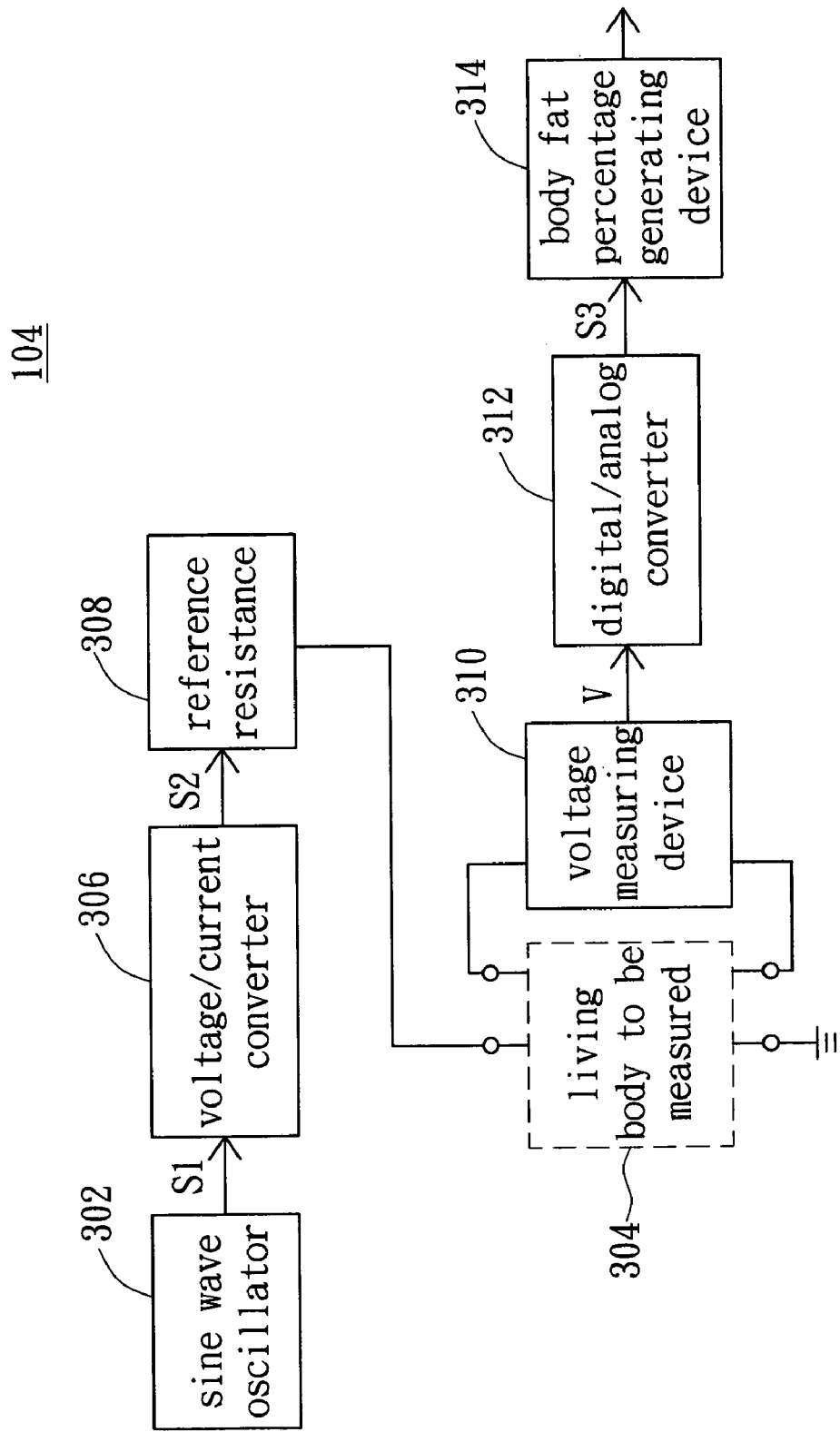
FIG. 3 is a detailed block diagram of the fat measuring control circuit illustrated in FIG. 1.

Referring to FIG. 3, a detailed block diagram of fat measuring control circuit 104 illustrated in FIG. 1 is shown. Fat measuring control circuit 104 includes a sine wave oscillator 302, a voltage/current converter 306, a reference resistance 308, a voltage measuring device 310, a digital/analog converter 312 and a body fat percentage generating device 314. Sine wave oscillator 302 is used to provide an alternating voltage signal S1; voltage/current converter 306 is used to convert alternating voltage signal S1 into alternating current signal S2; reference resistance 308 is coupled to voltage/current converter 306; voltage measuring device 310 is coupled to voltage measuring electrode pair 206A and 206B. When living body to be measured 304, a user for example, touches constant current electrode pair 204A and 204B and voltage measuring electrode pair 206A and 206B, alternating current signal S2 flows through reference resistance 308 and the user's body. Meanwhile, voltage measuring device 310 detects voltage V between the voltage measuring electrodes 206A and 206B. Digital/analog converter 312 is used to convert voltage V into digital data S3. Body fat percentage generating device 314 hence produces the user's fat mass body according to the converted digital data S3 and the inputted data of user's weight and height. The body fat percentage is generated by dividing the fat mass by the user's weight.

The various applications of the mobile phone with fat measuring function according to the invention are further disclosed below.

Application One: the user's body fat percentage can be wirelessly transmitted to a medical center via the mobile phone according to the invention. The user can even instantly receive professional advices and follow-ups from the medical center via a mobile phone. After a body fat percentage is obtained, the user can have this data transmitted to a medical center. Referring to the user's medical history, the medical center can provide the user with dietary and exercise advices so that the user can make appropriate adjustments conducive to personal health accordingly. Besides, according to the body fat percentage obtained, mobile phone control module 102 can directly choose one suggested exercise quantity or one suggested menu from these stored in memory device 112 and have the chosen suggested exercise quantity or the chosen suggested menu displayed on display device 114.

Application Two: the mobile phone with fat measuring function according to the invention can also communicate with the base station to utilize the value-added service provided by the telecommunication company which provides the user with information of healthy diets available in nearby restaurants. The telecommunication company stores the information regarding healthy diets available in restaurants of different areas beforehand, so as to be able to provide the user with the availability of healthy diets in nearby restaurants when requested by a user who has just measured his or her body fat percentage using a mobile phone with fat measuring function. The user finds it extremely convenient because he or she can have instant information regarding where and what to eat when the user is out and wants to dine there.

Figure 4:
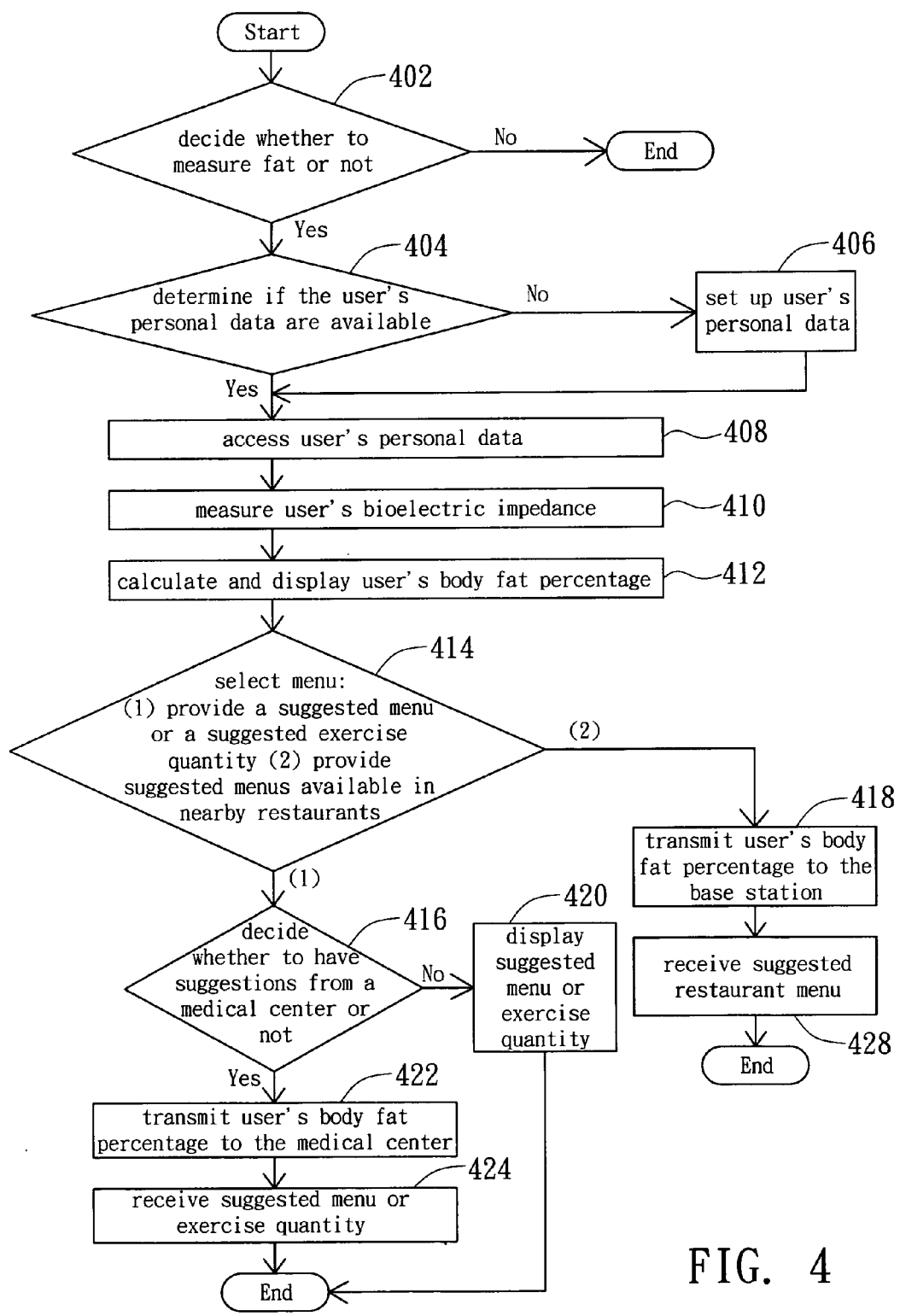
FIG. 4 is the flowchart of the first and the second applications of the mobile phone according to the invention.

Referring to FIG. 4, the flow chart illustrating the first and the second applications of the mobile phone according to the invention is shown. After mobile phone 100 is turned on, proceed to step 402 to decide whether to measure the fat or not; if yes, proceed to step 404, otherwise, terminate this process. In step 404, determine if the user's personal data are stored in memory device 112; if yes, proceed to step 408, otherwise, proceed to step 406 to set up user's personal data. In step 406, the user has to input at least his or her weight and height data. To make the data more complete, the user can input his or her gender and age as well. The user stores these data in memory device 112.

In step 408, mobile phone control module 102 accesses user's personal data from memory device 112. Next, proceed to step 410 to measure user's bioelectric impedance. After that, proceed to step 412 to produce user's body fat percentage and have the body fat percentage displayed on display device 114.

Following the above steps, proceed to step 414 which allows the user to choose either function (1), i.e. to provide a suggested menu or a suggested exercise quantity, or function (2), i.e. to provide information regarding the availability of suggested menu in nearby restaurants. Proceed to step 416 if function (1) is selected or proceed to step 418 if function (2) is selected.

In step 416, the user has to decide if he or she wants a medical center to provide suggested menu or suggested exercise quantity or not; if yes, proceed to step 422, otherwise, proceed to step 420. In step 422, mobile phone control module 102 transmits user's body fat percentage to the medical center. Then proceeds to step 424 where mobile phone control module 102 receives from the medical center a suggested menu or a suggested exercise quantity corresponding to his or her body fat percentage sent to the medical center earlier. After step 424, the process is terminated. In step 420, according to user's body fat percentage measured, mobile phone control module 102 directly chooses one suggested exercise quantity or one suggested menu from these stored in memory device 112 and have the chosen suggested exercise quantity or the chosen suggested menu displayed on display device 114. The process is then terminated.

In step 418, mobile phone control module 102 transmits user's body fat percentage to the base station. Next, proceed to step 428 where mobile phone control module 102 receives a menu corresponding to user's body fat percentage from the base station. The suggested menu contains the menu of diets available in nearby restaurants.

Figure 5:
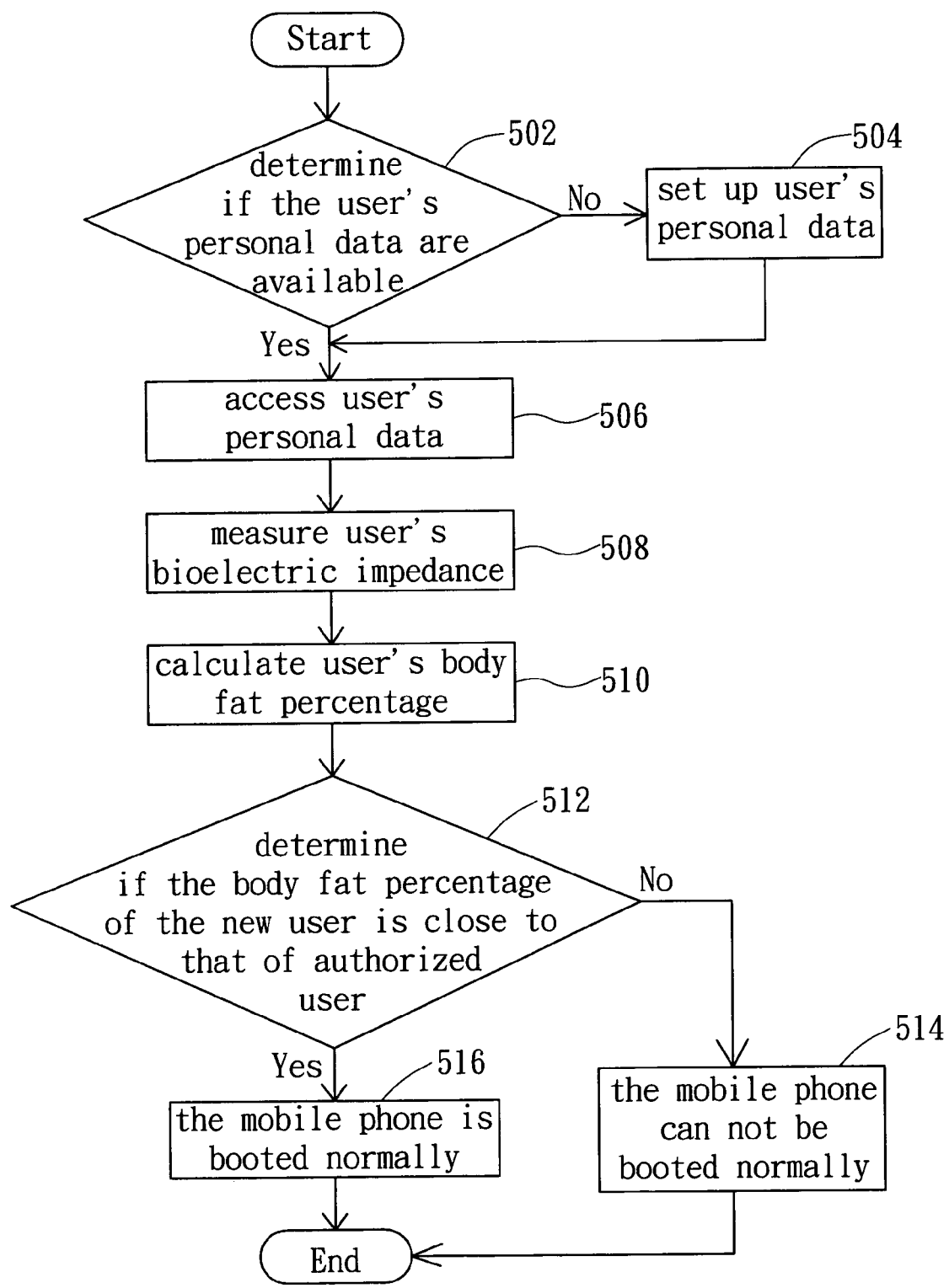
FIG. 5 is the flowchart of the third application of the mobile phone according to the invention.

Application Three: the mobile phone according to the invention is able to recognize user's identification. Memory device 112 of the mobile phone according to the invention can pre-store user's latest body fat percentage and define this body fat percentage as authorized user's body fat percentage. User's body fat percentage will be measured first before the normal booting procedure when the mobile phone is turned on next time. If the newly measured body fat percentage is very close to the last body fat percentage, say, within 3% tolerance error, the new user is identified as the original user and the mobile phone perform the normal booting procedure. The flowchart of the process is illustrated in FIG. 5.

Steps 502 to 510 are performed immediately after the mobile phone is turned on. Steps 502 to 510 are identical to steps 404 to 412 and are not to be repeated here. Next, perform step 512 to determine if the body fat percentage of the new user is close to that of the authorized user's. If not, proceed to step 514: the mobile phone terminates the normal booting procedure unless the unlocking passwords are inputted; if yes, proceed to step 516: the mobile phone performs the normal booting procedure of the mobile phone.

Figure 6:
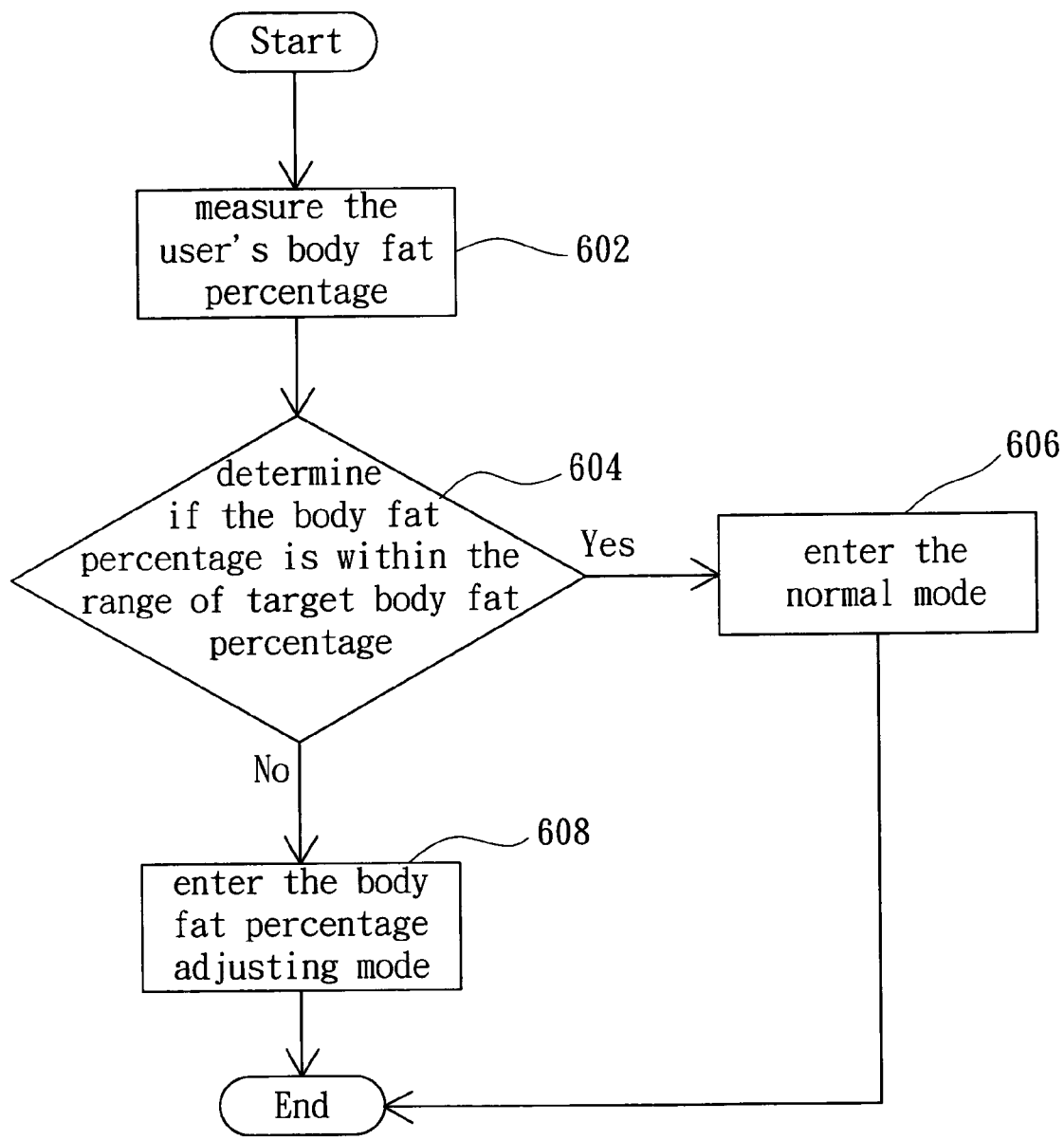
FIG. 6 is the flowchart of the fourth application of the mobile phone according to the invention.

Application Four. The mobile phone according to the invention can serve as a good reminder for the user to watch out for his or her dietary habit sand exercise quantities, as shown in FIG. 6. Memory device 112 according to the invention can store a predetermined range of target body fat percentage, e.g. the range considered to be normal for a healthy person. Every time when the user turns on the mobile phone, the mobile phone measures the user's body fat percentage again in step 602. After that, determination is made in step 604 if the body fat percentage is within the range of target body fat percentage. If the newly measured body fat percentage is within the range of target body fat percentage, mobile phone control module 102 directs the mobile phone to "normal mode", as shown in step 606.

If the newly measured body fat percentage is outside the range of target body fat percentage, although the mobile phone still can perform booting procedure successfully, the mobile phone control module 102 directs the mobile phone to "body fat percentage adjusting mode" exemplified below, as shown in step 608. (1) Mobile phone display device 114 displays some warning words or pictures to remind the user of dietary habits and exercise quantities, or the display device initiates a screen saver reminding the user of watching out for health. (2) The mobile phone imposes a restriction on the length of talk time allowed per day. (3) The mobile phone imposes a restriction on the number of calls the user can make per day.

The mobile phone continue to operate under "body fat percentage adjusting mode" and does not change to "normal mode" until the body fat percentage measured when turning on the mobile phone turns out to be within the target range. The screen pictures and restriction imposed on the user serve as a good reminder of watching out for personal health.

The mobile phone according to the invention can have only one or have all of the above applications at the same time.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A mobile phone for measuring a user's body fat percentage according to the user's weight data, comprising:
   a mobile phone control module;
   a display device coupled to the mobile phone control module;

a fat measuring control circuit coupled to the mobile phone control module;

a constant current electrode pair coupled to the fat measuring control circuit;

a voltage measuring electrode pair coupled to the fat measuring control circuit; and a memory device which is coupled to the mobile phone control module and stores a range of target body fat percentage set by the user, wherein when the user touches the constant current electrode pair and the voltage measuring electrode pair, the fat measuring control circuit applies a predetermined current to the constant current electrode pair, causing the voltage measuring electrode pair to generate a measured voltage, the user's body fat percentage is then generated according to the measured voltage and the user's weight data, and the body fat percentage is displayed on the display device, wherein the mobile phone control module selectively imposes restrictions on the length of talk time or the number of calls the user can make within a specific period of time if the user's body fat percentage is outside the target range.

2. A fat measuring method performed on a mobile phone, the mobile phone including a mobile phone control module, a display unit, a fat measuring control circuit, a constant current electrode pair, a voltage measuring electrode pair, and a memory device, both the display unit and the fat measuring control circuit being coupled to the mobile phone control module, both the constant current electrode pair and the voltage measuring electrode pair being coupled to the fat measuring control circuit, the memory device being coupled to the mobile phone control module and storing a range of target body fat percentage predetermined by a user, the method comprising the steps of:

accessing the user's personal data including at least a weight data by the mobile phone control module;

touching the constant current electrode pair and the voltage measuring electrode pair by the user, allowing the fat measuring control circuit to measure a bioelectric impedance of the user;

generating a body fat percentage of the user according to the bioelectric impedance and the user's personal data by the fat measuring control circuit, and displaying the body fat percentage on the display device; and determining if the user's body fat percentage is outside the range of target body fat percentage; if yes, selectively imposing restrictions on the length of talk time or the number of calls the user can make within a specific period of time by the mobile phone control module.

3. A mobile phone for measuring a user's body fat percentage according to the user's weight data, comprising:

a mobile phone control module;

a display device coupled to the mobile phone control module;

a fat measuring control circuit coupled to the mobile phone control module;

a constant current electrode pair coupled to the fat measuring control circuit;

a voltage measuring electrode pair coupled to the fat measuring control circuit; and a memory device which is coupled to the mobile phone control module and stores an authorized body fat percentage for the user, wherein when the user touches the constant current electrode pair and the voltage measuring electrode pair, the fat measuring control circuit applies a predetermined current to the constant current electrode pair, causing the voltage measuring electrode pair to generate a measured voltage, the user's body fat percentage is then generated according to the measured voltage and the user's weight data, and the body fat percentage is displayed on the display device, wherein the mobile phone control module terminates a normal booting procedure of the mobile phone if the user's body fat percentage measured by the mobile phone is beyond a tolerance error of the user's authorized body fat percentage.

4. A fat measuring method performed on a mobile phone, the mobile phone including a mobile phone control module, a display unit, a fat measuring control circuit, a constant current electrode pair, a voltage measuring electrode pair, and a memory device, both the display unit and the fat measuring control circuit being coupled to the mobile phone control module, both the constant current electrode pair and the voltage measuring electrode pair being coupled to the fat measuring control circuit, the memory device being coupled to the mobile phone control module and storing an authorized body fat percentage of a user, the method comprising the steps of:

accessing the user's personal data including at least a weight data by the mobile phone control module;

touching the constant current electrode pair and the voltage measuring electrode pair by the user, allowing the fat measuring control circuit to measure a bioelectric impedance of the user;

generating a body fat percentage of the user according to the bioelectric impedance and the user's personal data by the fat measuring control circuit, and displaying the body fat percentage on the display device; and determining if the body fat percentage measured by the mobile phone is beyond a predetermined tolerance error of the user's authorized body fat percentage; if yes, terminating a normal booting procedure of the mobile phone by the mobile phone control module.

* * * * *